United States Patent [19]

Trasch et al.

[11] Patent Number: 5,055,195
[45] Date of Patent: Oct. 8, 1991

[54] ERYTHROCYTE-RETENTION SUBSTRATES

[75] Inventors: Heinz-Friedrich Trasch; Erwin Endres, both of Ludwigshafen; Andreas Trost, Hockenheim; Walter Rittersdorf, Mannheim, all of Fed. Rep. of Germany

[73] Assignee: Boehringer Mannheim GMBH, Mannheim, Fed. Rep. of Germany

[21] Appl. No.: 77,003

[22] Filed: Jul. 20, 1987

Related U.S. Application Data

[63] Continuation of Ser. No. 619,940, Jun. 12, 1984, abandoned.

[30] Foreign Application Priority Data

Jul. 2, 1983 [DE] Fed. Rep. of Germany ....... 3323973

[51] Int. Cl.$^5$ .................... B01D 15/00; G01N 33/49; G01N 33/51
[52] U.S. Cl. .................... 210/638; 210/502.1; 210/639; 210/660; 210/692; 210/767; 422/56; 436/177
[58] Field of Search .................. 210/638, 639, 502.1, 210/692, 660, 767; 422/56, 58, 101; 436/170, 177, 178

[56] References Cited

U.S. PATENT DOCUMENTS

| 3,092,465 | 6/1963 | Adams et al. | 436/169 |
| 3,522,925 | 1/1971 | Fetter | 422/56 |
| 3,522,928 | 1/1971 | Fetter | 436/177 |
| 3,552,925 | 1/1971 | Fetter | 422/56 X |
| 3,630,957 | 12/1971 | Rey et al. | 422/56 |
| 4,144,306 | 3/1979 | Figueras | 422/56 |
| 4,340,565 | 7/1982 | Kitajima et al. | 422/56 |
| 4,363,874 | 12/1982 | Greenquist | 422/56 |
| 4,390,343 | 6/1983 | Walter | 422/56 |
| 4,477,575 | 10/1984 | Vogel et al. | 436/170 |

Primary Examiner—W. Gary Jones
Attorney, Agent, or Firm—Felfe & Lynch

[57] ABSTRACT

The present invention provides erythrocyte-retention substrates of the general formula:

$$R_1-Sp-R_2$$

in which Sp is a bridge serving as a spacer, $R_1$ is a strongly polar group and $R_2$ is also a strongly polar group or, when Sp is an electron-conductive group, $R_2$ can also be a polarizable group.

The present invention also provides a process for the separation of erythrocytes from whole blood, wherein whole blood is brought into contact with one of the above substrates and subsequently filtered through a filter layer and the separated plasma obtained.

18 Claims, 2 Drawing Sheets

ERYTHROCYTE-RETENTION SUBSTRATES

This application is a continuation of application Ser. No. 619,940, filed June 12, 1984, now abandoned.

The present invention is concerned with erythrocyte retention substrates and with a process for separating erythrocytes from whole blood.

In recent years, clinical chemical analysis processes have been developed in two directions, both of which are to be regarded from the point of view of reducing the expense. One direction is that of automisation and thus the rationalisation of analytical processes with which large numbers of samples and parameters are investigated in central laboratories in the shortest possible period of time. The other direction is the simplification and acceleration of analytical methods which the physician uses in the direct taking care of his patients. Especially those processes in which the results can, in practice, be obtained in the presence of the patients are of primary interest for ambulant attention for reasons of expense since the waiting times are thereby drastically reduced and the losses of time which result by requesting the patients to return after the analytical results have been obtained are practically overcome. For the rapid and simplest analysis of individual samples or of small series of samples, test strips have achieved particular importance in which the reagents are contained in a matrix of paper or synthetic resin and the sample is applied directly to this matrix since, with the introduction of reflection photometric processes, quantitative evaluations can also be made possible with outstanding precision and correctness.

The test strips hitherto commercially available for the determination of components of blood have, however, the following disadvantages. Most processes are disturbed by the erythrocytes. Before the analysis, the user must, therefore, separate the serum or plasma from whole blood by centrifuging. However, especially in the case of small amounts of sample, this is problematical. Only a few tests, in which the reagent layer itself (see Federal Republic of Germany Patent Specification No. 15 98 153) or a prepositioned membrane is semipermeable and retains the erythrocytes, can have whole blood applied thereto directly. However, in the case of these tests, the red blood colouring material must be removed by washing off or wiping off before carrying out a reflection photometric measurement. This method cannot be used in the case of large molecules, for example enzymes, since these are also retained by the semipermeable layer.

Attempts have certainly not been lacking in developing systems in which it is possible to work directly with whole blood and the separation of the erythrocytes or of the haemoglobin and thus the obtaining of the plasma takes place in the system itself. Multilayer test devices for blood, in which one or more layers act as a filter which retain the corpuscular components of the blood, are known, for example, from Federal Republic of Germany Patent Specification No. 2,222,951 and from U.S. Pat. No. 4,144,306. However, since, for the separation of the erythrocytes, membranes must be used with pores of 1 to 3 μm., these easily become blocked and retard the passage through of the plasma which thereby enters the reaction layer slowly and non-uniformly. An advance was achieved by the use of special glass fibre filters, such as are described in Federal Republic of Germany Patent Specification No. 3,029,579. Such glass fibre filters can be used especially well for the production of test strips for the analysis of blood. The particulate blood components are therebhy separated off from the plasma in the simplest possible way when whole blood is applied to a glass fibre fleece which retains the erythrocytes and sucks up the plasma via a capillary fleece (transport fleece) which then transports it to the reagent layer in which the detection reaction take place.

These systems have proved to be very useful but, nevertheless, they also have certain disadvantages. The dead volume of the erythrocyte retention zone is, corresponding to the test construction and the separation capacity, relatively high. The ratio of the plasma separated off to the amount of blood used is, therefore, unfavourable and, in the case of blood samples with comparatively high haematocrit values, is further impaired. Therefore, amongst other things, it can happen that the separation system is not able to deal with the amount of erythrocytes to be separated so that blood colouring matter gets into the reaction zone and there brings about distrubances.

In U.S. Pat. Nos. 3,552,925 and 3,552,928, there are described inorganic salts and amino acids which are said to be suitable for coagulating the blood to such an extent that it is retained in a normal filter paper. The concentrations used of the salts (1 molar) and of the amino acids (5%) bring about only a relatively weak separation of the erythrocytes and plasma but already a considerable degree of haemolysis so that they are not suitable for obtaining plasma in test strips.

Therefore, the problem exists of finding retention substrates which, in concentrations at which haemolysis does not occur, bring about a strong coagulation of the blood so that the corpuscular components are effectively retained in a paper or glass fibre fleece and are separated from the plasma.

Surprisingly, we have now found that this object can be achieved by bringing the blood to be investigated into contact with retention substrates which contain two strongly polar groups which are connected bhy a non-polar bridge which serves as a spacer and contains 2 to 20 carbon or nitrogen atoms. It is assumed that these substrates are able to change the polarity of the surface of the erythrocytes and to cause these to coagulate. The formation of agglomerates in the blood by the addition of the retention substrates can easily be observed microscopically.

As erythrocyte retaining substrates, there are used compounds of the general formula:

$$R_1—Sp—R_2,$$

in which Sp is a bridge serving as a spacer, $R_1$ is a strongly polar group and $R_2$ is also a strongly polar group or, when SP is an electron-conducting group, can also be a polarisable group.

The substituents $R_1$ and $R_2$ can thereby be the same or different and signify $SO_3H$, COOH, $NH_2$ or OH, especially in ionic form, and $R_2$ can also be an $NO_2$, $SO_2NH—$, CONH—group, a halogen atom or an alkyl radical.

Sp preferably signifies an aromatic of heteroaromatic ring system with at least two rings, which are annelated or connected either directly or via —CH=CH—, —N=N—, —CR$_3$=N—, —NR$_3$—CO—NR$_4$—or —CR$_3$R$_4$—, in which $R_3$ and $R_4$ are hydrogen atoms or alkyl radicals. Especially preferred are those ring systems in which $R_1$ $R_2$ are present on different rings and still further substituents with the same meaning as $R_1$, as well as $NO_2$, halogen, alkoxy, alkyl, $SO_2$, $NR_3$ and $CONR_3$, can possibly also be present. Also preferred are aliphatic diamines with 2 to 10 and preferably 2 to 6 carbon atoms. The groups $R_1$ and $R_2$ are preferably present in ionised form, since the corresponding compounds are, on the one hand, better soluble in water and, on the other hand, the higher polarity of the ions improves the retention properties Alkyl or Alkoxy in all occurencies means a straight, branched or cyclic radical with 1-10, preferably 1-6 C-atoms, especially a methyl or ethyl group.

The retention substrates are preponderantly dyestuffs and belong to the most varied classes of substances, for example acidic dyestuffs, basic dyestuffs, direct dyestuffs, mordant dyestuffs, reactive dyestuffs and optical brighteners, but can also be compounds without a dyestuff character, for example aliphatic diamines.

Naturally, not all retention substrates are equally suitable for each test. Thus, some materials bring about a partial haemolysis which can be disturbing in the case of some chemical reactions. In the same way, some retention substrates enter into undesired exchange reactions with enzymes. Both effects cannot be derived directly from the structure but such materials are easy to determine by simple experiments. Therefore, they cannot be used for the corresponding test. However, the large selection of possible retention substrates contains a sufficient number of suitable representatives for each test. Naturally, the selection of the retention substrates must take place in such a manner that the inherent colour thereof does not falsify the reaction colour of the test, which is possible due to the great variety of the classes of compounds which can be used. The retention substrates manifest their effectiveness not only in solution but also when they are firmly attached to the carrier, for example in the case of the use of direct dyestuffs on cellulose-containing carriers. The above-mentioned reactive dyestuffs can admittedly react with the carriers but this is not essential since their effectiveness is also manifest when they can be leached out of the fibres.

The suitability of a substrate can easily be determined in a simple screening experiment in which either the blood is mixed with 0.5 to 1% of the substrate and thereafter applied with a capillary to a retention matrix, for example a filter paper of glass fibre fleece, where the erythrocytes separate out around the point of application and a ring of clear plasma spreads out outwardly. In the case of useful substrates, this outer ring is at least twice and preferably three times as great as the erythrocyte-containing zone. For serial tests, it is more appropriate to use another experiment in which a 1 to 5% solution of the substrate is impregnated on a thin paper which is laid upon a larger fleece or paper serving as a retention zone or filter. When whole blood is applied to the first paper, it becomes enriched with the substrate so that the erythrocytes are separated out in the retention zone and a clear plasma front spreadsout.

The retention substrates according to the present invention can be used in a large variety of different ways. The nature of the use depends upon the construction and flow scheme of the analysis system in which it is desired to employ the retention substrates. A series of possible embodiments is described in Federal Republic of Germany Patent Specification No. 3,029,579. Further variations can be developed by the expert without difficulty.

Figure 1:
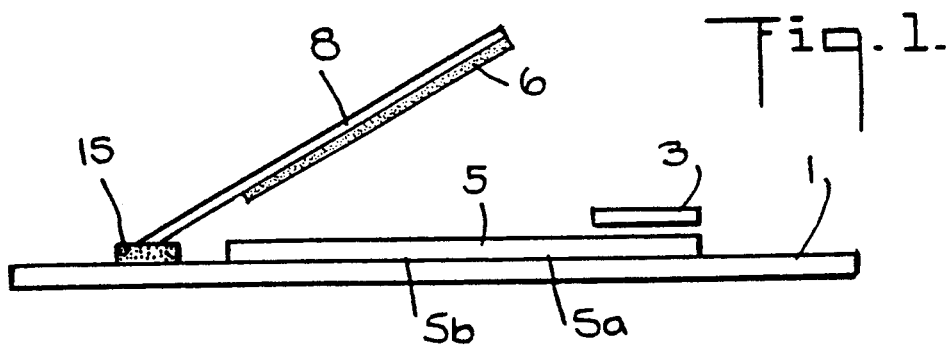
FIGS. 1-7 show various embodiments of the analysis system device of the invention.

Referring to the drawings the analysis system device of FIG. 1 is the most preferred embodiment of the device. On a film strip 1 is applied a strip 5 of an absorbent material and over a part 5b of this material is present a dry reagent carrier 8, a reagent zone 6 of which is impregnated with reagents for the detection of, for example, glucose, urea, uric acid, GOT, gamma-GT or other substrates or enzymes. The carrier is so fixed to the film 1 at a point of adhesion 15 that 6 can be brought into contact with 5b by pressure from above. Over another part 5a of the absorbent material 5, there is present an erythrocyte retention zone 3 which contains the retention substrate. The blood sample is pipetted on to the retention system 3. The red blood colouring material or the erythrocytes which disturb the detection process are retained in 3 and 5a and the plasma passes through the absorbent transport material 5 into the region 5b under the reagent zone 6. After the region 5b has filled with plasma, the reagent zone 6 is pressed upon it and thereby wetted with plasma. The detection reaction takes place and the resultant colour is assessed visually or measured remission photometrically.

The retention substrate can be held either directly in 3 or can be applied thereover on an additional (not illustrated) absorbent or non-absorbent, permeable carrier.

As absorbent material for the retention zone 3 which is provided with the retention substrates, there can, in principle, be used all absorbent, porous carriers of filters which are premeable to liquids, for example papers, fleeces, gels, fabrics and the like made of cellulose, wool, glass fibre, asbestos, synthetic fibres, polymers or mixtures thereof, which are suitable for separating agglomerated erythrocytes, i.e. materials the pore sizes of which are greater than individual erythrocytes, i.e. approximately 10 to 100 $\mu$.

Non-absorbent materials for the additional substrate carrier include, for example, meshes of coarse fibres. The loading of the carrier with the retention substrates takes place by simple impregnation thereof from aqueous or organic solutions. Film-forming or adhesion-promoting substances, for example gelatine, alginates and other natural products, as well as water-soluble synthetic compounds, for example poly-vinylpyrrolidones and the like, can also be added to the solutions, as well as buffers, surface-active substances and other adjuvants, insofar as these do not promote haemolysis of the blood and do not disturb the subsequent test reaction.

The transport material 5 is preferably a glass fibre fleece, since this only displays minor exchange reactions with the plasma, but this can also be replaced by other capillary-active materials, for example filter paper insofar as these give up sufficient plasma to the reagent zone 6. Further suitable materials can be determined experimentally without difficulty.

It is of especial advantage already previously to add the retention substrate to the blood, preferably during the taking of a blood sample. The blood sampling device then contains the retention substrate in solid form, for example on the inner wall of the sampling device, or dissolved in physiological sodium chloride solution in a suitable container. By means of a comparatively long contact time with the retention substrate, the coagulation of the erythrocytes is intensified to such an extent that a comparatively small retention zone 3 suffices and the plasma yield is improved.

The following Examples are given for the purpose of illustrating the present invention:

EXAMPLE 1

Production of a test strip for the detection of glucose in the blood

Figure 2:
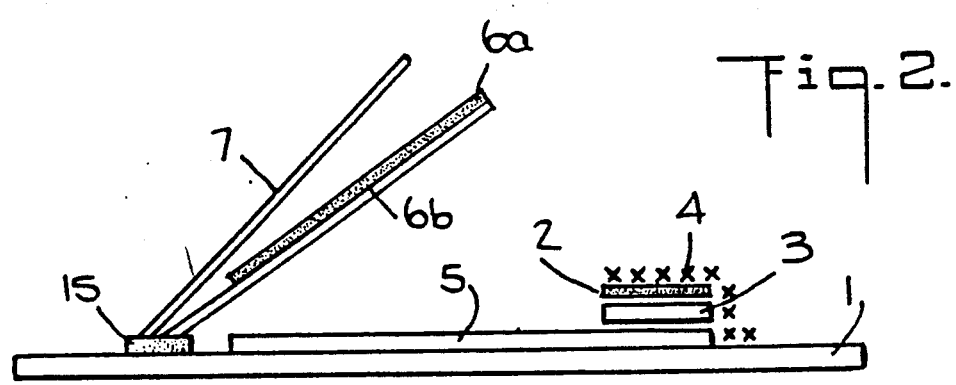

35 KU glucose oxidase
200 KU peroxidase
15 ml. 0.5M phosphate buffer, pH 5
0.3 g. sodium alginate
25 g. dispersion of a mixed polymer of vinyl acetate and vinyl propionate (50% in water)
0.5 g. 3,3',5,5'-tetramethylbenzidine
0.2 g. phenyl semicarbazide
1 g. dioctyl sodium sulphosuccinate
6 ml. methoxyethanol
20 g. titanium dioxide
35 ml. water were worked up to give a homogeneous mass and coated with a width of 0.1 mm. on to a 250 μ thick multifilar polyamide fabric (2F 131 Schweizer Seidengaze-Fabrik) and dried. The so obtained reagent zone 6 with the reagent film 6a was thereafter attached to a transparent covering film 7 so that the covering film lay against the reagent film 6a. Subsequently, a 1 cm. wide strip of this coated fabric 6, with the fabric side 6b below, was fixed, according to FIG. 2 of the accompanying drawings, at a point of adhesion 15 on to a plastics strip 1 on which there had already been applied a 15 mm. wide glass fibre fleece 5 of 0.25 mm. thickness and with a weight per surface area of about 25 g./m²., so that the free end of the coated fabric extended 6 mm. over the fleece (zone 5b). The separating system was applied to the glass fibre fleece. It consisted of a glass fibre fleece 3 with a thickness of 1 mm. and a substrate carrier 2 (stencil paper, schöller und Hösch, weight per unit surface area 12 g./m²), impregnated with a 5% aqueous solution of Remazol Yellow GNL, which was connected with the plastics strip 1 by a nylon mesh 4. When 30 μl. of whole blood were applied to the nylon mesh 4, then, within a short period of time, the blood passed through the whole separation system and mixed with the retention substrate, which resulted in the agglomeration of the erythrocytes. The agglomerated erythrocytes were retained and the plasma migrated to the transport fleece 5 under the fabric 6b coated with the reagent film 6a.

By applying pressure to the cover film 7, the reagent zone 6 was then contacted, via the fabric side 6b with the separated plasma and was uniformly moistened. The glucose present in the plasma reacted within 1 to 2 minutes, depending upon its concentration, with the development of a more or less strong blue colour, which was measured remission photometrically at 630 nm. Results obtained with the above-described test strip are given in the following Table.

| mg./dl glucose | % remission |
| --- | --- |
| 0 | 75 |
| 80 | 62 |
| 150 | 44 |
| 210 | 40 |
| 300 | 35 |
| 400 | 30 |

If, in the above-described Example, the stencil paper impregnated with Remazol Yellow GNL is omitted, then the erythrocytes migrate so far in the transport fleece that they lead to disturbances in the case of a remission photometric measurement of the test field.

EXAMPLE 2

Production of a test strip for the detection of bilirubin in blood 0.2 g. 2-methoxy-4-nitrobenzenediazonium tetrafluoroborate
1.5 g. metaphosphoric acid
1.5 g. diphenylphosphoric acid
0.2 g. dioctyl sodium sulphosuccinate
5 g. silica gel
1 g. cellulose
7.5 g. polyvinylidene chloride dispersion (Diofan 217 D, BASF) (40% in water)
15 g. swelling agent (Bentone EW, National Lead) (2.5% in water)

were worked up to give a homogeneous mass and coated with a width of 0.2 mm. on to a 200 μm. thick, multi-filar polyester fabric (2 F 777, Schweizer Seidengaze-Fabrik) and dried.

The coated carrier so obtained was worked up as described in Example 1 to give a test strip but the substrate carrier 2 was impregnated with a 5% solution of the sodium salt of naphthalene-2,6-disulphonic acid.

The reaction with bilirubin-containing blood took place as described in Example 1 and, after a reaction time of 60 seconds, gave an excellent gradation over the whole of the relevant concentration range.

EXAMPLE 3

Production of a test strip for the detection of cholesterol in blood 2.5 KU cholesterol oxidase
1.5 KU cholesterol esterase
50 KU peroxidase
10 mg. gallic acid
0.5 g. 3,3',5,5'-tetramethylbenzidine
0.3 g. dioctyl sodium sulphosuccinate
1.5 ml. acetone
6.5 g. dispersion of a mixed polymer of vinyl acetate and vinyl propionate (50% in water)
5 g. titanium dioxide
10 g. cellulose
15 ml. phosphate buffer, 0.5M, pH 7
20 ml. water were worked up to give a homogeneous mass and coated with a width of 0.15 mm. on to a 140 μm. thick poly-carbonate film and dried.

Figure 3:
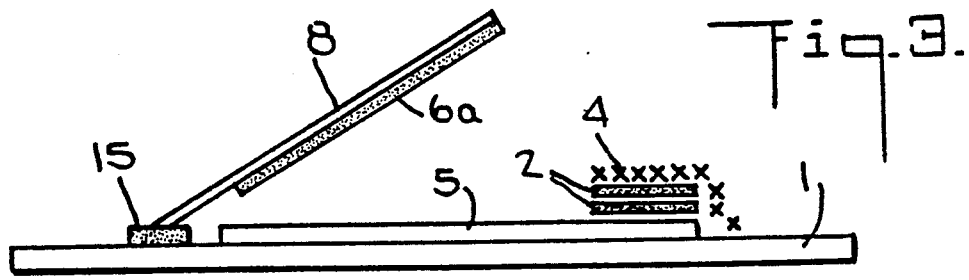

The reagent carrier 8 so coated was worked up as described in Example 1 to give test strips, the covering film being omitted, and the coated film, arranged with reagent film below, replaced the fabric. In the separation system, the glass fibre fleece 3 was replaced by a further piece of stencil paper (FIG. 3).

For the detection of cholesterol in blood, two pieces of tea bag paper (Schöller and Hösch, weight per unit surface area 12 g./m²), impregnated with 5% Remazol Yellow FGH in water, were used.

The reaction with cholesterol-containing blood took place by pressing the coated film on to the transport fleece filled with plasma. The separated plasma thus reached the reagent film, moistened it and, after a reaction time of 100 seconds, gave an excellent gradation over the whole of the relevant concentration range.

EXAMPLE 4

Production of a test strip for the detection of triglycerides in blood

50 KU peroxidase
20 KU cholesterol esterase
50 KU glycerol kinase
10 KU glycerophosphate oxidase
20 g. dispersion of a mixed polymer of vinyl acetate and vinyl propionate (50% in water)
20 g. cellulose
0.2 g. sodium alginate
10 g. titanium dioxide
0.68 g. 3,3',5,5'-tetramethylbenzidine
0.30 g. dioctyl sodium sulphosuccinate
1.5 ml. acetone
25 ml. phosphate buffer, 0.2M, pH 7.8
10 ml. water
0.2 g. adenosine triphosphate
were worked up to give a homogeneous mass and coated with a width of 0.2 mm. on to a 140 μm. thick polycarbonate film and dried. The coated carrier so obtained was worked up as described in Example 3 to give a test strip. The reaction with triglyceride-containing blood took place as in Example 3 and, after a reaction time of 120 seconds, gave an excellent gradation over the whole of the relevant concentration range.

As transport fleece 5, there was used filter paper (Schleicher und Schüll, No. 0858). The retention zone 3 consisted of a mixed fibre fleece (VS 532, Binzer), impregnated with 5% Naphthol Yellow S.

EXAMPLE 5

Production of a test strip for the detection of uric acid in blood

40 KU peroxidase
1 KU uricase
18 g. dispersion of a mixed polymer of vinyl acetate and vinyl propionate (50% in water)
0.25 g. sodium alginate
0.5 g. non-ionic wetting agent
0.05 g. disodium ethylenediamine-tetraacetate
20 g. kieselguhr
20 ml. phosphate buffer, 0.2M, pH 7
0.4 g. primaquine diphosphate
18 ml. water
were worked up to give a homogeneous mass and coated with a width of 0.2 mm. on to a 150 μm. thick polyester film and dried.

Indicator paper

A thin filter paper (597 NF-Ind., Schleicher und Schüll) was impregnated with a solution consisting of 0.2 g. 4-aminoantipyrine and 0.2 g. of a non-ionic wetting agent in 50 ml. water and dried.

Figure 4:
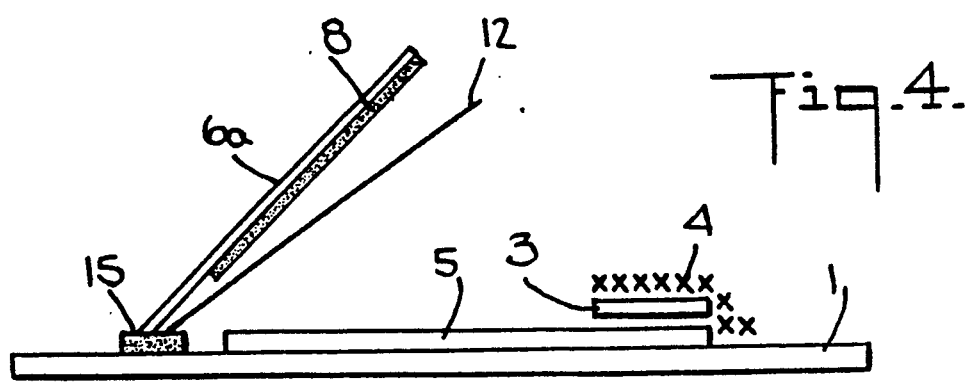

Test strips were produced in the manner described in Example 3 which, between the transport fleece and the reagent film lower side, contained a layer of the aminoantipyrine paper 12 (FIG. 4).

The uric acid-containing blood was obtained with a sampling device which, upon sampling, mixed the blood with Solidazol Brilliant Yellow 4G. The so treated blood was applied to the protective mesh 4 of the test strip and, after a reaction time of 120 seconds, gave an excellent gradation over the whole of the relevant concentration range.

EXAMPLE 6

Production of a test strip for the detection of gamma-glutamyl transferase in blood 1.0 g. N-methylanthranilic acid
2.5 g. glycylglycine
0.85 g. disodium ethylenediamine-tetraacetate
0.2 g. glutamyl-p-phenylenediamine-3-carboxylic acid
20 g. dispersion of a mixed polymer of vinyl acetate and vinyl propionate (50% in water)
0.2 g. sodium alginate
0.35 g. dioctyl sodium sulphosuccinate
1.0 ml. methanol
5 g. titanium dioxide
8 g. cellulose
15 ml. tris buffer, pH 7.6
15 ml. water
were worked up to give a homogeneous mass and coated in a width of 0.15 mm. on to a 250 μm. thick multi-filar polyamide fabric (1093 Verseidag-Industrie-Textilien GmbH) and dried.

A tea bag paper (Schöller und Hösch, weight per unit surface area 12 g./cm$^2$) was impregnated with 250 mmol/liter potassium ferricyanide and dried at 30° C. for 5 minutes. Test strips were prepared as described in FIG. 3. The retention zone 3 consisted of a piece of tea bag paper 2, impregnated with the sodium salt of anthraquinone-2,6-disulphonic acid (5% in water) as retention substrate, and a piece of tea bag paper 2 impregnated with potassium ferricyanide (5% in water).

The reaction with gamma-GT-containing blood took place as in Example 1 and, after a reaction time of 120 seconds, gave an excellent gradation over the whole of the relevant concentration range.

Figure 5:
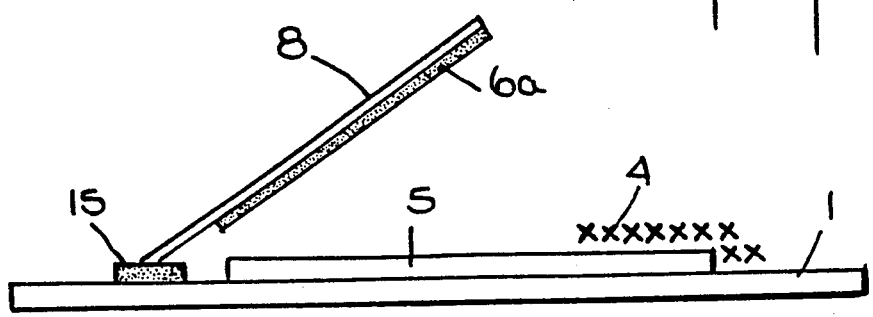

FIG. 5 shows a further test strip variant in which the separation system as described in the previous Examples was omitted and, in place thereof, there was used the transport paper 5 impregnated with the retention substrate Remazole Brilliant Yellow GL. In the case of the use of blood pre-treated, for example, with 1% Direct Yellow 62 or Thiazole Yellow G, the same test strip arrangement can be used as in FIG. 5 but the transport system (paper, glass fibre fleece . . .) did not need to be impregnated.

EXAMPLE 7

Production of a test strip for the detection of glutamate-pyruvate transaminase in blood A) Enzyme paper 0.2 mol/liter morpholine-ethanesulphonic acid/potassium hydroxide, pH 6.5
0.8 mol/liter alanine
$0.5 \times 10^{-3}$ mol/liter thiamine pyrophosphate
$10 \times 10^{-3}$ mol/liter magnesium chloride
$1 \times 10^{-3}$ mol/liter potassium hydrogen phosphate
20 KU/liter peroxidase
200 KU/liter pyruvate oxidase.

A tea bag paper (Schöller und Hösch, weight per unit surface area 12 g./m$^2$) was impregnated with this solution and dried at 30° C. for 5 minutes.

B) Indicator paper $10 \times 10^{-3}$ mol/liter 4-(4-dimethylaminophenyl)-2-(3,5-dimethoxy-4-hydroxyphenyl)imidazole
$18 \times 10^{-3}$ mol/liter α-ketoglutaric acid
were dissolved in 0.1 mol/liter hydrochloric acid. A tea bag paper (Schöller und Hösch, weight per unit surface area 12 g./m²) was impregnated with this solution and dried at 30° C. for 5 minutes.

Figure 6:
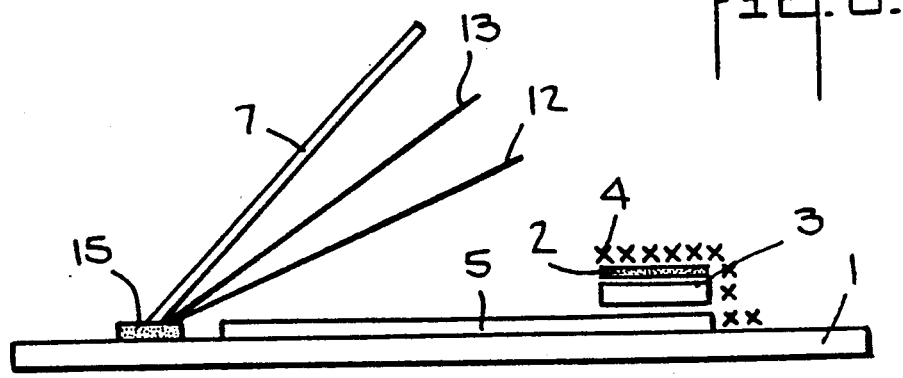

Working up to give test strips took place as described in Example 1, the reagent zone 6 being replaced by the two impregnated papers 12 and 13 (FIG. 6). The reaction with GPT-containing blood took place by pressing the covering film 7 on to the transport fleece 5 filled with plasma. Plasma migrated through the indicator paper 12 into the enzyme paper 13 and, within the course of 2 minutes, gave an excellent gradation over the whole of the relevant concentration range.

As retention zone 3, there was used a stencil paper (Schöller und Hösch, weight per unit surface area 12 g./m²) impregnated with Acid Yellow 25, in combination with a filter paper (Schleicher und Schüll, No. 1406).

EXAMPLE 8

Simple experiment for testing for the suitability of retention substrates

Figure 7:
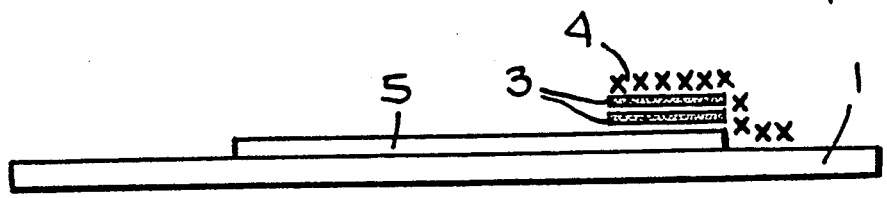

As illustrated in FIG. 7, on to a plastics strip 1 of 10 cm. length and 6 mm. breadth, there is stuck a 15 mm. long glass fibre transport fleece 5 (weight per unit surface area 25 g./m²). On one end of the transport fleece, there were fixed, as retention zone 3, two pieces of 6×6 mm. stencil paper (Schöller und Hösch, weight per unit surface area 12 g./m²) by means of a protective mesh 4 so that the impregnated pieces of stencil paper were completely covered. When 30 μm. whole blood were then applied to the protective mesh, the blood penetrated through the two pieces of stencil paper and mixed with the retention substrate. The blood then entered the transport fleece by migrating in a capillary manner, the erythrocytes thereby being retained. Suitable retention substrates are present when the erythrocyte travelling distance is shorter than in the case of comparative measurements with non-impregnated pieces of paper. The travelling distance was measured 1 minute after application of the whole blood, after the transport fleece was completely filled with plasma.

The stencil paper was impregnated with 3 to 5% (w/v) solutions and dried at 35° C. for 30 minutes. The length of the travelling distance was, to a small degree, dependent upon the blood used.

In the following, there is given a list of substances which can be used as retention substrates when measurement is carried out in the range of 600 to 650 nm by reflection photometry. In brackets there is given, as far as known, the Colour Index Number or the chemical name.

| erythrocyte distance traversed in test model, in mm. | retention substrate |
| --- | --- |
| 5 | control without impregnation |
| 3 | Primazin yellow GRL (reactive yellow 15) (BASF) |
| 3 | Levafix brilliant yellow E3G (reactive yellow 25) (Bayer) |
| 1.5 | Levafix E-R2 (reactive yellow 26) (Bayer) |
| 1.5 | Levafix gold yellow EG (reactive yellow 27) (Bayer) |
| 2 | Naphthol yellow S (2,4-dinitro-1-naphthol-7-sulphonic acid disodium salt) |
| 2.5 | Chrysophenin G extra (direct yellow 12) |
| 1.5 | Blancophor G (fluorescent brightener 40) (Bayer) |
| 2 | Blancophor REU (fluorescent brightener 119) (Bayer) |
| 2.5 | Blancophor RA (fluorescent brightener 204) (Bayer) |
| 2.5 | Blancophor R (fluorescent brightener 30) (Bayer) |
| 2 | Blancophor CE (fluorescent brightener 118) (Bayer) |
| 3 | Blancophor BE (fluorescent brightener 115) (Bayer) |
| 2.5 | Blancophor BA 267 (fluorescent brightener 113) (Bayer) |
| 0.5 | Blancophor BBH (Bayer) |
| 0.5 | Blancophor RPA (fluorescent brightener 148) (Bayer) |
| 0.5 | Blancophor BBU (fluorescent brightener 114) (Bayer) |
| 1 | Tinopal BV (fluorescent brightener 1) (Geigy) |
| 3 | Tinopal UP (fluorescent brightener 154) (Geigy) |
| 2 | Uvitex NB (fluorescent brightener 183) (Ciba) |
| 1.5 | Uvitex RT (fluorescent brightener 37) (Ciba) |
| 3 | Uvitex CF (fluorescent brightener 134) (Ciba) |
| 1.5 | Ultraphor WT (fluorescent brightener 48) (BASF) |
| 1.5 | naphthalene-2,6-disulphonic acid, sodium salt |
| 1.0 | 1-naphthol-3,6-disulphonic acid, sodium salt |
| 1.0 | anthraquinone-2,6-disulfonic acid, sodium salt |
| 2.5 | Rivanol (2-ethoxy-6,9-diaminoacridine) (Hoechst) |
| 1.5 | Chrysoidine HR (basic organge 2) (Hoechst) |
| 2.5 | Primazin brilliant yellow 3-GL (reactive yellow 37) (BASF) |
| 0.5 | Remazol yellow FG (reactive yellow 42) (Hoechst) |
| 0.5 | Remazol yellow G (reactive yellow 14) (Hoechst) |
| 0.5 | Remazol yellow GNL (reactive yellow 23) (Hoechst) |
| 0.5 | Remazol yellow FGH (reactive yellow 42:1) (Hoechst) |
| 0.5 | Remazol brilliant yellow GL (reactive yellow 37) (Hoechst) |
| 0.5 | Solidazol brilliant yellow 4G (reactive yellow 40) (Cassella) |
| 2.5 | Brilliant yellow (direct yellow 4) |
| 1.5 | Brilliant sulphaflavine (acid yellow 7) |
| 1.5 | 4,4'-diaminostilbene-2,2'-disulfphonic acid, sodium salt |
| 1.5 | 4-nitro-4'-aminostilbene-2,2'-disulphonic acid, sodium salt |
| 2.5 | 2-(4-aminophenyl)-6-methyl-benzothiazole-7-sulphonic acid, sodium salt |
| 0.5 | Acid yellow 17 (food yellow 5) |
| 0.5 | Acid yellow 23 (tartrazine) |
| 0.5 | Acid yellow 25 |
| 2.0 | Acid yellow 34 |
| 2.5 | Acid yellow 38 |
| 1.5 | Acid yellow 40 |
| 1.5 | Acid yellow 65 |
| 1 | Acid yellow 76 |

| erythrocyte distance traversed in test model, in mm. | retention substrate |
|---|---|
| 1 | Acid yellow 99 |
| 0.5 | Mordant Orange 10 (3-methyl-5-[4-(4-sulphonobenzeneazo)-benzeneazo]-salicylic acid, sodium salt) |
| 2.5 | Mordant yellow 3R (5-(p-nitrobenzeneazo)-salicylic acid, sodium salt) |
| 0.5 | Mordant yellow 7 (5-(p-sulphobenzeneazo)-3-methylsalicylic acid, sodium salt) |
| 1.5 | Mordant yellow 10 (5-(p-sulphobenzeneazo)-3-methylsalicylic acid, sodium salt) |
| 0.5 | Mordant yellow 12 (5-(p-aminobenzeneazo)-3-methylsalicylic acid, sodium salt) |
| 1.5 | Direct yellow 8 (acid yellow 186) |
| 0.5 | Direct yellow 27 (C.I. 13950) |
| 1.5 | Direct yellow 29 (C.I. 19556) |
| 0.5 | Direct yellow 50 (C.I. 29025) |
| 0.5 | Direct yellow 62 (C.I. 36900) |
| 0.5 | Direct orange 31 (C.I. 23655) |
| 1 | Basic yellow 11 (C.I. 48055) |
| 1.5 | Alizarine yellow R (mordant orange 1, C.I. 14030) |
| 1.5 | Alizarine yellow GG (mordant yellow 1, C.I. 14025) |
| 1 | Thiazole yellow (C.I. 19540) |
| 0.5 | Primulin (direct yellow 59, C.I. 4900) |
| 0.5 | Direct yellow 11, (C.I. 40000) |
| 0.5 | Acid yellow 9 (C.I. 13015) |
| 2–3 | 1,6-diaminohexane |
| 2–3 | 1,4-diaminobutane |
| 2.5–3 | 1,3-diaminopropane |
| 2–3 | 1,2-diaminoethane |
| — | 1,6-diaminohexane.2 HCl |
| — | 1,4-diaminobutane.2 HCl |
| — | 1,3-diaminopropane.2 HCl |
| — | 1,2-diaminoethane.2 HCl |
| 5 | 4,4-dihydroxybiphenyl |
| 5 | 2,3-diaminonaphthalene |
| 1 | 1,8-diaminonaphthalene |
| 3,5–4.5 | 1,5-diaminonaphthalene (90–92%) |
| 5 | hexane-1,6-diol |
| 5 | succinic acid (5%) |
| 3.0 | succinic acid, disodium salt (5%) |
| 5 | butane-1-sulphonic acid, sodium salt (5%) |
| 4 | 1,4-dinitrobenzene (5%) |
| 4 | 4,4-dinitrostilbene (5%) |
| 1.5 | 4,4-diaminostilbene.2 HCl |
| 1.5 | anthraquinone-2,6,disulphonic acid, sodium salt |
| 5 | 2,6-dihydroxyanthraquinone |

Comparative experiment according to U.S. Pat. Specification No. 3,552,928

| | |
|---|---|
| 4–5 | cysteine hydrochloride.H$_2$O |
| 5 | tyrosine sodium salt |
| 3 | L-proline sodium salt |
| 3 | alanine sodium salt |
| 3–4 | L-asparagine sodium salt |
| 3–4 | L-arginine sodium salt |
| 4–5 | tryptophane sodium salt |

Comparative experiment according to U.S. Pat. Specification No. 3,552,925

| | |
|---|---|
| 3–4 | zinc sulphate, haemolysis |
| 0.5 | potassium chloride, strong haemolysis |
| 2.5 | sodium acetate, strong haemolysis |

It will be understood that the specification and examples are illustrative but not limitative of the present invention and that other embodiments within the spirit and scope of the invention will suggest themselves to those skilled in the art.

What is claimed is:

1. Analysis system device for determination of a component of blood plasma comprising:

(a) a separation means for separating plasma from whole blood, wherein said separation means contains an erythrocyte retention substrate of formula $R_1$—$S_p$—$R_2$, where $S_p$ is a bridge serving as a spacer and is an aromatic or hetero aromatic ring system comprising at least two rings which are either annelated or connected together directly or through a link selected from the group consisting of —CH=CH—, —N=N—, —CR$_3$=N—, —NR$_3$—CO—NR$_4$, and —CR$_3$R$_4$—, wherein R$_3$ and R$_4$ are hydrogen or alkyl;

R$_1$ is SO$_3$H, COOH, NH$_2$ or OH; and

R$_2$ is SO$_3$H, COOH, NH$_2$, OH, NO$_2$, SO$_2$NH, CONH, halogen or a straight, branched, or cyclic alkyl with 1–10 carbon atoms, or both R$_1$ and R$_2$ are amino groups or amino groups in salt form and Sp is an alkylene radical with 2 to 10 carbon atoms, (b) a conducting means for conducting plasma into an analysis zone, (c) an analysis zone separate from said separation means and said conducting means, which contains an analysis reagent for determining said component, and (d) a filter means operable to retain the erythrocytes while the separated plasma is conducted to said analysis zone.

2. System of claim 1, wherein $S_p$ is an aromatic or heteroaromatic ring system with at least two rings, which rings are either annelated or are connected directly or through a link selected from the group consisting of —CH=CH—, —N=N—, —CR$_3$=N—, NR$_3$—CO—NR$_4$— or —CR$_3$R$_4$—, wherein R$_3$ and R$_4$ are hydrogen or alkyl, R$_1$ and R$_2$ being positioned in different rings.

3. System of claim 1, wherein the ring system contains at least one further substituent selected from the group consisting of SO$_3$H, COOH, NH$_2$, alkylamino, dialkylamino, OH, NO$_2$, halogen, alkoxy, alkyl, or CONH$_2$.

4. System of claim 1, wherein R$_1$ and R$_2$ are amino groups or amino groups in salt form, and $S_p$ is an alkylene radical with 2 to 10 carbon atoms.

5. System of claim 1, wherein $S_p$ is an alkylene radical of 2 to 6 carbon atoms.

6. Process for separating erythrocytes from whole blood comprising contacting whole blood with a separation means containing an erythrocyte retention substrate of formula $R_1$—$S_p$—$R_2$, where $S_p$ is a bridge serving as a spacer and is an aromatic or hetero aromatic ring system comprising at least two rings which are either annelated or connected together directly or through a link selected from the group consisting of —CH=CH—, —N=N, —CR$_3$=N—, —NR$_3$—CO—NR$_4$, and —CR$_3$R$_4$— wherein R$_3$ and R$_4$ are hydrogen or alkyl;

R$_1$ is SO$_3$H, COOH, NH$_2$ or OH; and

R$_2$ is SO$_3$H, COOH, NH$_2$, OH, NO$_2$, SO$_2$NH, CONH, halogen or a straight, branched, or cyclic alkyl with 1–10 carbon atoms, or both R$_1$ and R$_2$ are animo groups or animo groups in salt from and Sp is an alkylene radical with 2 to 10 carbon atoms so as to separate erythrocytes from whole blood.

7. Process of claim 6, further comprising filtering blood from which erythrocytes have been separated to obtain plasma therefrom.

8. Process of claim 6, wherein the substrate contacts the whole blood in a layer preceding a filter layer.

9. Process of claim 6, wherein the substrate contacts the whole blood in a filter layer.

10. Process of claim 9, wherein the substrate is bound to a matrix of the filter layer.

11. Process of claim 6, wherein the substrate is added to the whole blood.

12. Process for separating erythrocytes from whole blood, comprising contacting whole blood with a separating means containing an erythrocyte retention substrate which is a non hemolyzing dye so as to separate erythrocytes from whole blood.

13. Process of claim 12, further comprising filtering blood from which erythrocytes have been separated to obtain plasma therefrom.

14. Process of claim 12, wherein the substrate contacts the whole blood in a layer preceding a filter layer.

15. Process of claim 12, wherein the substrate contacts the whole blood in a filter layer.

16. Process of claim 15, wherein the substrate is bound to a matrix of the filter layer.

17. Process of claim 12, wherein the substrate is added to the whole blood.

18. Analysis device for determination of a component of blood plasma comprising:
  (a) a separation means for separating plasma from whole blood, wherein said separation means contains an erythrocyte retention substrate which is a non hemolyzing dye;
  (b) a conducting means for conducting plasma into an analysis zone;
  (c) an analysis zone separate from said separation means and said conducting means, which contains an analysis reagent for determining said component, and
  (d) a filter means operative to retain the erythrocytes while the separated plasma is conducted to the analysis zone.

* * * * *